US011351521B2

(12) United States Patent
Gong et al.

(10) Patent No.: US 11,351,521 B2
(45) Date of Patent: Jun. 7, 2022

(54) SUPPORTED CORE-SHELL BIMETALLIC CATALYST WITH HIGH SELECTIVITY FOR PROPANE DEHYDROGENATION

(71) Applicant: TIANJIN UNIVERSITY, Tianjin (CN)

(72) Inventors: Jinlong Gong, Tianjin (CN); Weiting Cai, Tianjin (CN); Rentao Mu, Tianjin (CN); Liang Zeng, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 399 days.

(21) Appl. No.: 16/604,559

(22) PCT Filed: Apr. 20, 2018

(86) PCT No.: PCT/CN2018/083832
§ 371 (c)(1),
(2) Date: Oct. 10, 2019

(87) PCT Pub. No.: WO2018/192559
PCT Pub. Date: Oct. 25, 2018

(65) Prior Publication Data
US 2020/0122122 A1 Apr. 23, 2020

(30) Foreign Application Priority Data
Apr. 22, 2017 (CN) .......................... 201710273775.X

(51) Int. Cl.
*B01J 23/42* (2006.01)
*B01J 23/745* (2006.01)
(Continued)

(52) U.S. Cl.
CPC ............... *B01J 23/42* (2013.01); *B01J 23/74* (2013.01); *B01J 29/0333* (2013.01);
(Continued)

(58) Field of Classification Search
CPC . B01J 23/42; B01J 23/745; B01J 23/75; B01J 23/755; B01J 23/8906;
(Continued)

(56) References Cited

U.S. PATENT DOCUMENTS 5,702,836 A * 12/1997 Ma .................... H01M 4/921
429/506
8,178,463 B2 * 5/2012 Stamenkovic ........ H01M 4/921
502/101
(Continued)

FOREIGN PATENT DOCUMENTS

| CN | 102746087 A | 10/2012 |
|----|-------------|---------|
| CN | 103028400 A | 4/2013 |

(Continued)

*Primary Examiner* — Cam N. Nguyen
(74) *Attorney, Agent, or Firm* — Bayramoglu Law Offices LLC

(57) ABSTRACT

A supported core-shell bimetallic catalyst with high selectivity, and preparation method and an application thereof are provided. SBA-15 is used as support, platinum (Pt) is used as active component, 3d transition metal is used as cocatalysts. In the core-shell bimetallic catalyst formed by the 3d transition metal and Pt, in one aspect, by the addition of the 3d metal in the core, the d-band center of surface Pt atoms is down shifted, and the absorption of propylene is weakened, thereby improving the selectivity for propylene. In another aspect, the use of Pt is reduced by the addition of the 3d transition metal, improving the utilization of Pt. The catalyst is applicable in a hydrogen atmosphere, has a good effect on the preparation of propylene by propane dehydrogenation and causes high dehydrogenation activity under high temperature conditions. The total selectivity for propylene may reach 85%, which achieves high propylene selectivity.

13 Claims, 6 Drawing Sheets

(51) Int. Cl.
*B01J 23/75* (2006.01)
*B01J 23/755* (2006.01)
*B01J 23/89* (2006.01)
*B01J 35/00* (2006.01)
*B01J 29/03* (2006.01)
*C07C 5/333* (2006.01)
*C07C 11/06* (2006.01)
*B01J 23/74* (2006.01)

(52) U.S. Cl.
CPC ......... *B01J 35/0046* (2013.01); *C07C 5/3337* (2013.01); *C07C 11/06* (2013.01); *B01J 2229/18* (2013.01); *C07C 2529/03* (2013.01)

(58) Field of Classification Search
CPC .. B01J 23/8913; B01J 23/892; B01J 35/0046; B01J 29/0333; C07C 5/3337; C07C 11/06
See application file for complete search history.

(56) References Cited

U.S. PATENT DOCUMENTS

| | | | | |
|---|---|---|---|---|
| 8,685,878 B2* | 4/2014 | Stamenkovic | ........ | H01M 4/921 502/101 |
| 8,709,969 B2* | 4/2014 | Lin | ...................... | B01J 35/0013 502/339 |
| 8,815,272 B2* | 8/2014 | Woo | ...................... | B01J 37/0211 424/421 |
| 8,871,672 B2* | 10/2014 | Goto | ...................... | H01M 4/925 502/325 |
| 9,017,576 B2* | 4/2015 | Biausque | .................. | B22F 9/24 252/373 |
| 9,040,449 B2* | 5/2015 | Semagina | ............... | B01J 23/468 502/300 |
| 9,163,041 B2* | 10/2015 | Wan | ......................... | B01J 23/70 |
| 9,259,724 B2* | 2/2016 | Pan | ...................... | B01J 37/0244 |
| 9,469,535 B2* | 10/2016 | Biausque | .................. | B22F 9/24 |
| 9,614,228 B2* | 4/2017 | Hayden | ............... | H01M 4/9075 |
| 10,016,751 B2* | 7/2018 | Monnier | .................. | B01J 23/42 |
| 10,454,114 B2* | 10/2019 | Fang | ...................... | H01M 4/921 |
| 10,537,881 B2* | 1/2020 | Li | ............... | B01J 21/04 |
| 11,088,371 B2* | 8/2021 | Fang | ...................... | H01M 4/926 |
| 2008/0220296 A1* | 9/2008 | Eichhorn | ............... | H01M 4/925 429/437 |
| 2011/0189589 A1* | 8/2011 | Erlebacher | ............... | H01M 4/92 429/523 |
| 2011/0250122 A1* | 10/2011 | Joo | ......................... | B01J 23/42 423/437.2 |
| 2020/0129973 A1* | 4/2020 | Wang | .................... | B01J 23/8913 |

FOREIGN PATENT DOCUMENTS

| | | |
|---|---|---|
| CN | 104084198 A | 10/2014 |
| WO | 2016072755 A1 | 5/2016 |

* cited by examiner

SUPPORTED CORE-SHELL BIMETALLIC CATALYST WITH HIGH SELECTIVITY FOR PROPANE DEHYDROGENATION

CROSS REFERENCE TO RELATED APPLICATIONS

This application is the national phase entry of International Application No. PCT/CN2018/083832, filed on Apr. 20, 2018, which is based upon and claims priority to Chinese Patent Application No. 201710273775.X, filed on Apr. 22, 2017, the entire contents of which are incorporated herein by reference.

TECHNICAL FIELD

The present invention relates to a method for preparing a catalyst with high selectivity for a dehydrogenation of propane to propylene and an application thereof. More specifically, the present disclosure relates to a Santa Barbara Amorphous-15 (SBA-15) supported catalyst with a PtFe@Pt core-shell structure, a preparation method thereof and its effect on propylene selectivity for a dehydrogenation of propane into propylene.

BACKGROUND

Bimetallic catalysts exhibit superior catalytic performance during numerous catalytic reactions compared to single metal catalysts. The stability, activity and selectivity of bimetallic catalysts can be greatly improved by adjusting the structures, compositions and shapes of the bimetallic catalysts. Designing and synthesizing bimetallic catalysts with special structures and compositions is one of the effective ways to improve the catalytic performance. For example, platinum (Pt) is widely used in various catalytic reactions due to its superior catalytic properties. However, Pt is very expensive, and thus it is important to reduce the usage of Pt. Adding other metals can modify the metal Pt, and at the same time decrease the amount of Pt used. In heterogeneous catalysis, only the surface atoms of metal nanoparticles function as the catalyst. By adding other transitional metals in the subsurface layer and utilizing the difference in surface free energy, a core-shell structure where Pt is enriched on the surface is formed. By the electronic effect and geometric effect between the transition metal and Pt, the d-band center of the Pt atoms is downshifted, and the catalytic reaction performance of the Pt atoms on the surface is improved. Meanwhile, the addition of the transition metals help reaching the objective of reducing the Pt usage. For example, the activity of the catalytic oxidation reaction of carbon monoxide can be utterly improved by a special synthetic sandwich structure whose subsurface has Ni, wherein the presence of the subsurface Ni downshifts the d-band center of the surface Pt atoms, and thus carbon monoxide is absorbed in smaller amounts than typically expected. In oxygen reduction reaction (ORR) reaction processes, the PtCualloy@Pt core-shell structure is synthesized, the ORR reaction activity of the surface Pt atoms is improved via the electronic and geometric effects of Cu, and the use of Pt is also reduced.

Propylene, as one of the most important chemical products and raw materials, can be used to synthesize chemical products such as acrylonitrile, polypropylene, and propylene oxide. However, in traditional production processes of propylene, problems such as high energy consumption, poor selectivity, and scarce oil resources are presented. To solve these problems, it is necessary to find an economical and efficient production method of preparing propylene. Recently, the method of preparing propylene by propane dehydrogenation (PDH) has become more prevalent. About 5 million tons of propylene per year are produced via PDH processes. In the PDH processes, Pt-based catalysts have been widely used in the industry due to its excellent reactivity. Nonetheless, on one hand, the high cost and scarcity of Pt have given rise to extended research attempting to increase the utilization of Pt. On the other hand, obviously, the PDH process ($C_3H_8 \leftrightarrows C_3H_6+H_2 \Delta H_{298K}=124.3$ kJ/mol) is endothermic and is limited by thermodynamic equilibrium. High temperatures and low pressure are conducive to this reaction. However, excessive high temperatures may result in coke deposits and may decrease selectivity for propene. Hence, another urgent problem to be solved is to design and synthesize a special and effective catalyst to weaken the adsorption of propylene intermediates and increase the selectivity for propylene.

SUMMARY

In accordance with the objectives of this invention, this disclosure relates to addressing the shortcomings in the art and improve pure Pt catalyst's selectivity for propene. The core-shell bimetallic catalyst Pt3d@Pt/SBA-15 with high selectivity for propylene is prepared by steps such as impregnation, high-temperature reduction in hydrogen, and acid leaching. The catalyst is applied to processes of propane dehydrogenation. By adding 3d transition metal atoms, the d-band center of surface Pt atoms is downshifted, the deposition of pure Pt in the high-temperature reaction process is inhibited, thereby improving the selectivity for propylene and increasing the catalytic performance of Pt.

The technical objectives of the present invention are realized by the following technical solutions.

A supported core-shell bimetallic catalyst with high selectivity includes metal Pt and 3d metal loaded on a support. For the mass of the support of 100 wt %, the content of platinum ranges from 0.5 wt % to 1 wt %, preferably 0.75 wt %-0.8 wt % (i.e., metal platinum mass/support mass). The mole ratio of the metal Pt to the 3d metal is about (3-5):(0.75-1), preferably 3:(0.75-0.85). A shell layer composed of the metal Pt is formed on the surface of the catalyst. An inner core composed of the metal Pt and the 3d metal is formed in the catalyst. Moreover, from the surface to the inner core, the content distribution of the metal Pt gradually decreases, and the content distribution of the 3d metal (Fe, Co and Ni) gradually increases.

The support is commercial SBA-15. The 3d metal is Fe, Co or Ni.

A method for preparing the supported core-shell bimetallic catalyst with high selectivity includes the following steps.

Step 1, adding the support to an impregnation system and then stirring and impregnating the system until the solvent in the impregnation system evaporates thoroughly to load the metal Pt and the 3d metal on the support to the impregnation system.

In step 1, the support is commercial SBA-15.

In step 1, the 3d metal is Fe, Co or Ni.

In step 1, the stirring and impregnating of the system are performed by a mechanical or ultrasonic agitator for 20-24 hours, with a speed of 200-300 revolutions per minute at 20-25° C.

In step 1, the impregnation system is composed of deionization water, ethanol and an aqueous of metal precursors, wherein the volume ratio of deionization water to ethanol is (1-2):(1-3), preferably 1:1; in the aqueous of metal precursors, the mole ratio of the metal Pt to the 3d metal is (3-5):(1-1.5), preferably 3:(1-1.5) or (3-5):1; for the mass of the support of 100 wt %, the content of Pt ranges from 0.5 wt % to 1 wt %, preferably 0.75 wt %-0.8 wt %.

Step 2, dry the support loaded with the metal Pt and the 3d metal, and then calcine in the air to form metal oxides at 300-350° C. for 2-4 hours with the ramp rate of 2-5° C./min from the room temperature of 20-25° C.

In step 2, the drying is performed in an oven at 50-70° C. for 10-12 hours, followed by grinding into powder.

Step 3: a high temperature reduction is carried out on the support obtained in step 2 in an atmosphere of hydrogen and argon at 400-450° C. for 4-6 hours with the ramp rate of 2-5° C./min from the room temperature of 20-25° C. In the mixed gas of hydrogen and argon, the volume percentage of hydrogen is 5-10%.

During the high temperature reduction in step 3, regarding the different thermodynamics and surface free energy between metal Pt and the 3d metal (Fe, Co, or Ni), the metal Pt with lower surface free energy tends to enrich the surface of the material, whereas the 3d metal (Fe, Co or Ni) tends to enrich in the core of the material. In this way, from the surface to the core of the material, the metal Pt exhibits an opposite distribution trend to the 3d metal (Fe, Co or Ni). The content distribution of the metal Pt is gradually decreased, and the content distribution of the 3d metal (Fe, Co or Ni) is gradually increased.

Step 4: performing an acid treatment on the high temperature reduced catalyst in step 3 to remove the 3d metal at the surface, thereby forming the shell layer composed of the metal Pt and the inner core composed of the metal Pt and the 3d metal.

In step 4, the acid used in the acid treatment can dissolve the 3d metal but does not react with the metal Pt, such as $5 \times 10^{-4}$ mol/L of a dilute nitric acid solution. The acid treatment is performed at 20-25° C. and lasts 1-20 minutes, preferably 10-20 minutes. 0.3 g of the reduced catalyst is added into 15 ml of the $5 \times 10^{-4}$ mol/L dilute nitric acid solution and followed by ultrasonic shaking for 30 seconds. The solid in the dilute nitric acid solution is segregated by centrifugation, then washed 3-5 times with deionized water. The catalyst after being washed and removed from the supernatant is dried at 60-80° C. in an oven for 10-12 hours.

An application of the supported core-shell bimetallic catalyst with high selectivity in propane dehydrogenation.

During use, the catalyst is subjected to a pelleting treatment to obtain the granular catalyst with a 20-40 mesh size distribution for subsequent use.

During use, the catalyst is loaded into a reactor and the mixed gas of nitrogen and hydrogen is introduced. The temperature is increased from the room temperature of 20-25° C. to 600-620° C. with the ramp rate of 3-5° C./min. The reduction of the catalyst at 600-620° C. lasts at least 0.5 hours, preferably 1-2 hours. In the mixed gas of nitrogen and hydrogen, the hydrogen is 10-15% by volume. After the reduction, the temperature in the reactor is controlled to be 550-650° C. Propane is introduced into the reactor at a weight hourly space velocity (WHSV) of 3-10 $h^{-1}$ for reaction, wherein the molar ratio of propane to hydrogen is 1:1, the equilibrium gas is nitrogen, and the volume ratio of propane, hydrogen and nitrogen is 7:7:11.

Compared with the prior art, the technical solution of the present invention has the following advantages.

(1) In the catalyst of the present invention, SBA-15 is used as a support, Pt is used as an active component, the 3d transition metal is used as a co-catalyst to modify and improve catalytic reaction performance of the surface Pt. The bimetallic catalyst with a special core-shell structure is formed by the 3d transition metal and Pt. In one aspect, the d-band center of the surface Pt atoms is downshifted by the addition of the 3d transition metal and the adsorption of propylene is weakened, making the propylene easier to desorb, thereby promoting the selectivity for propylene. On the other hand, by the addition of the 3d the transition metal, the objective of reducing Pt usage is achieved, the decrease of Pt usage is realized, and the high utilization of Pt is obtained.

(2) The catalyst of the present invention is suitable for use in a hydrogen atmosphere and has good effects on dehydrogenation of propane to propylene. The dehydrogenation activity is high under high temperature conditions, and the total selectivity for propylene is up to 85%, and the objective of high selectivity for propylene is achieved.

DETAILED DESCRIPTION OF THE EMBODIMENTS

Figure 1:
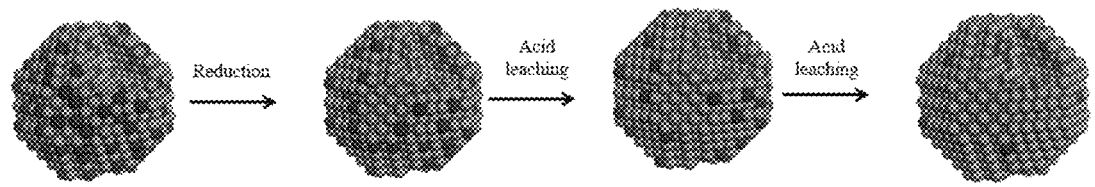
FIG. 1 is a schematic diagram of the technical solution of the present invention, where gray ball represents Pt atom, and black ball represents the 3d metal atom.
Figure 2:
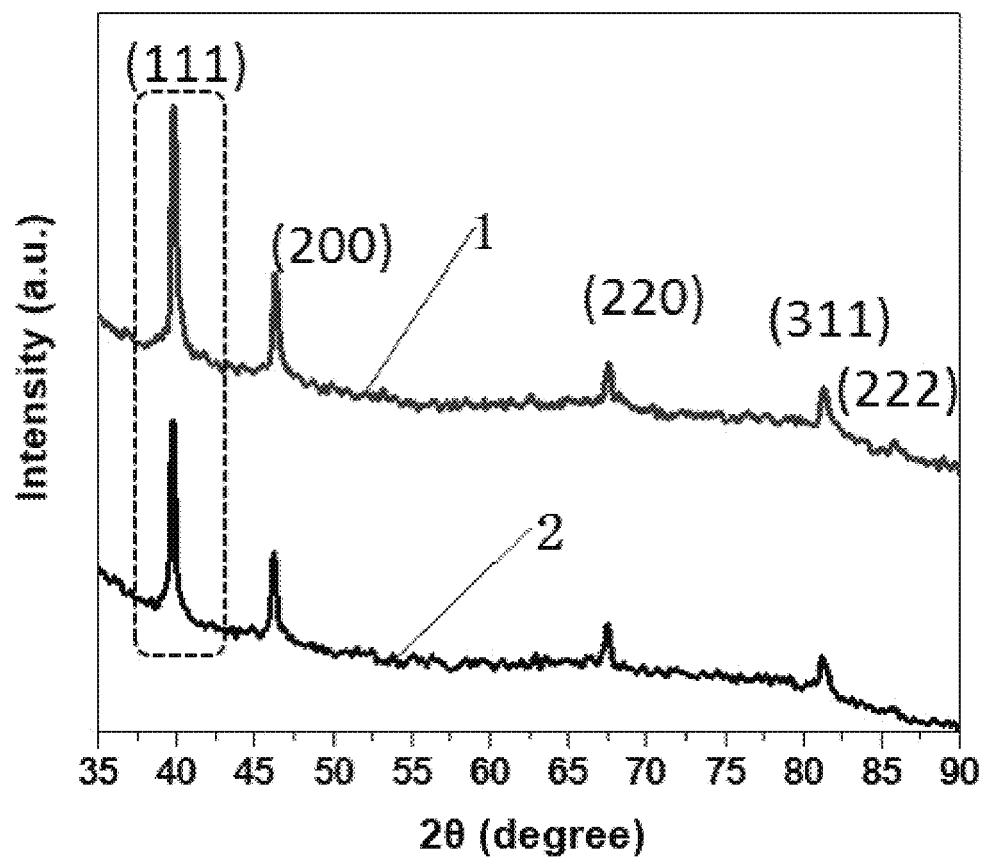
FIG. 2 shows first X-ray diffraction (XRD) patterns of the catalysts in the present invention, where line 1 presents the PtFe@Pt/SBA-15 catalyst of the present invention, and line 2 presents the Pt/SBA-15 catalyst.
Figure 3:
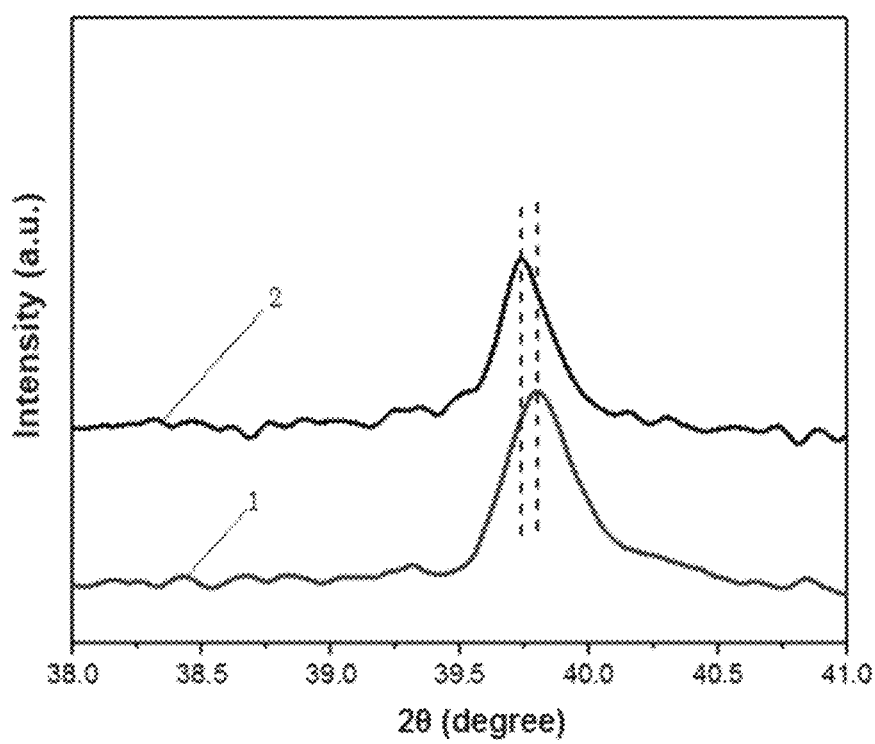
FIG. 3 shows second X-ray diffraction (XRD) patterns of the catalysts in the present invention, where line 1 presents the PtFe@Pt/SBA-15 catalyst of the present invention, and line 2 presents the Pt/SBA-15 catalyst.

The present invention is further described in detail below by specific embodiments. The core-shell bimetallic catalyst composed of Pt and 3d transition metal is supported on SBA-15, which is named as Pt3d@Pt/SBA-15 (3d=Fe, Co, or Ni).

Embodiment 1

(1) 5 mL of deionized water and 6 mL of ethyl alcohol were stirred in a beaker and mixed evenly. 0.75 mL of the prepared chloroplatinic acid (H$_2$PtCl$_6$) solution (0.010 g/mL) and the prepared Fe(NO$_3$)$_3$ solution were added to obtain a mixed solution, wherein the molar ratio of Pt to Fe is 3:1, and stirring was continued. At this time, 1 g of SBA-15 was added into the stirred solution.

(2) After stirring for 24 hours, the solution was gelatinized, and the beaker was placed in an oven for drying at 80° C. for 12 hours.

(3) The dried solid was ground to powder form, placed in a crucible and calcined in a muffle furnace at 300° C. for 2 hours at the ramp of 2° C./min.

(4) The calcined catalyst was placed in a high temperature resistant quartz boat, and placed in a tube furnace, 5% mixed gas composed of H$_2$ and Ar was introduced, and the reduction was performed at 400° C. for 4 hours at the ramp of 2° C./min.

(5) 0.3 g of the reduced catalyst was added into a dilute nitric acid solution at the concentration of 5×10$^{-4}$ mol/L, and ultrasonically shaken for 30 seconds. After shaking the solution, it was left for 10 minutes. Then the catalyst was separated by centrifuge process and washed three times with deionized water. The washed catalyst from which the supernatant was removed was dried at 60° C. for 12 hours in the oven. The obtained core-shell bimetallic catalyst composed of Pt and the 3d transition metal supported on the SBA-15 had a molecular formula of leached PtFe@Pt/SBA-15-10 min.

(6) The powder of the leached PtFe@Pt/SBA-15-10 min catalyst was pelleted to granular catalyst with a 20 to 40 mesh size distribution.

(7) The pelleted leached PtFe@Pt/SBA-15-10 min catalyst was loaded into a fixed reactor. The mixed gas of nitrogen and hydrogen was introduced, and the catalyst was pre-reduced at 600° C. for 1 hour, where the volume ratio of hydrogen to the mixed gas of nitrogen and hydrogen is 10%.

(8) After the reduction, the temperature at the bed layer of the reactor was controlled to 600° C. Propane is introduced into the reactor at the weight hourly space velocity (WHSV) of 10 h$^{-1}$, where the mole ratio of propane to hydrogen was 1:1 with nitrogen balanced, and the volume ratio of propane, hydrogen and nitrogen was 7:7:11.

Propane conversion, propylene selectivity and propylene yield were determined by equations as follows:

propane conversion:

$$Conv(\%) = \frac{[F_{C_3H_8}]_{in} - [F_{C_3H_8}]_{out}}{[F_{C_3H_8}]_{in}} \times 100$$

propylene selectivity:

$$Sel(\%) = \frac{3 \times [F_{C_3H_6}]_{out}}{3 \times [F_{C_3H_6}]_{out} + 2 \times [F_{C_2H_4}]_{out} + 2 \times [F_{C_2H_6}]_{out} + [F_{CH_4}]_{out}} \times 100$$

propylene yield:

$$Yield(\%) = \frac{Conv(\%) \times Sel(\%)}{100}$$

The reaction product was analyzed by an online gas chromatograph. The initial selectivity for propylene before and after adding Fe in the core when acid leaching for 10 minutes is shown in TABLE 1.

TABLE 1

The influence of Fe atoms at subsurface (i.e., 3d metal is added into internal layer) on propylene selectivity during propane dehydrogenation

| Catalysts | Pt/SBA-15 | PtFe@Pt/SBA-15 |
|---|---|---|
| Initial propylene selectivity (%) | 69 | 84 |

Figure 4:
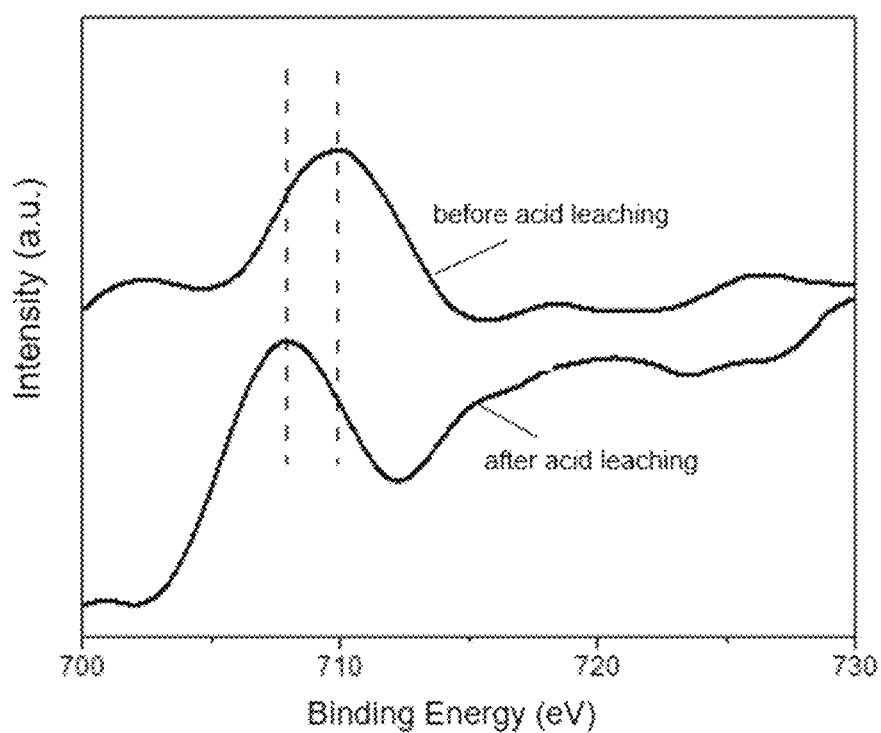
FIG. 4 is a schematic diagram of X-ray photoelectron spectroscopy (XPS) peaks of Fe2p before and after acid leaching.
Figure 5:
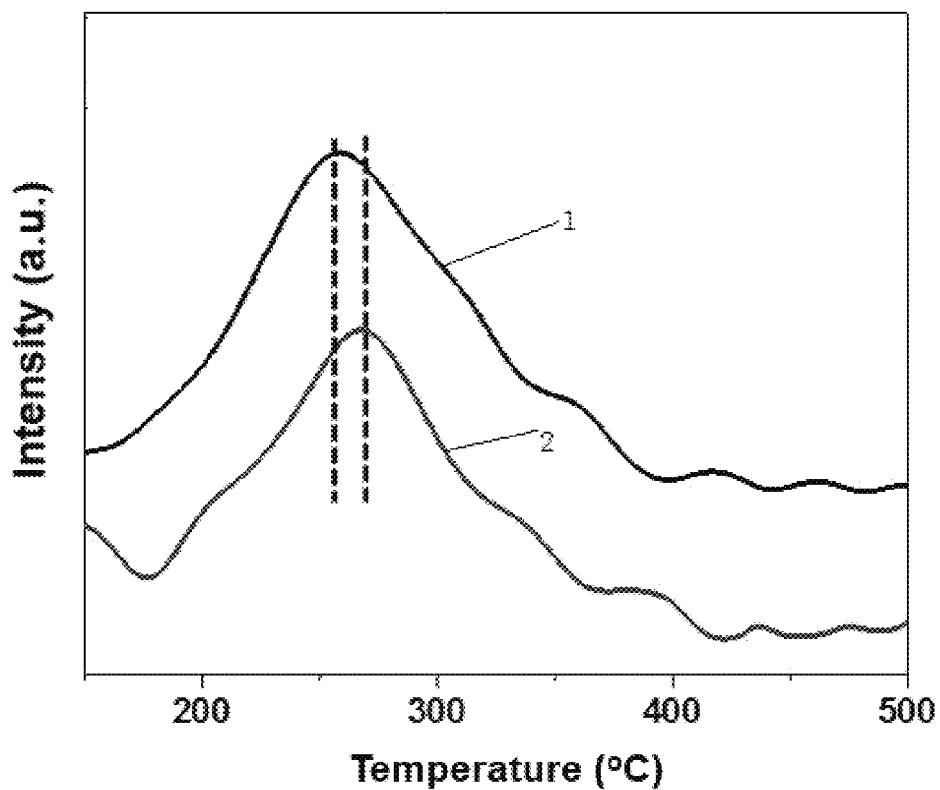
FIG. 5 shows curves of temperature-programmed desorption of propylene ($C_3H_6$-TPD) of the catalyst in the present invention, where line 1 presents the PtFe@Pt/SBA-15 catalyst of the present invention, and line 2 presents the Pt/SBA-15 catalyst.
Figure 6:
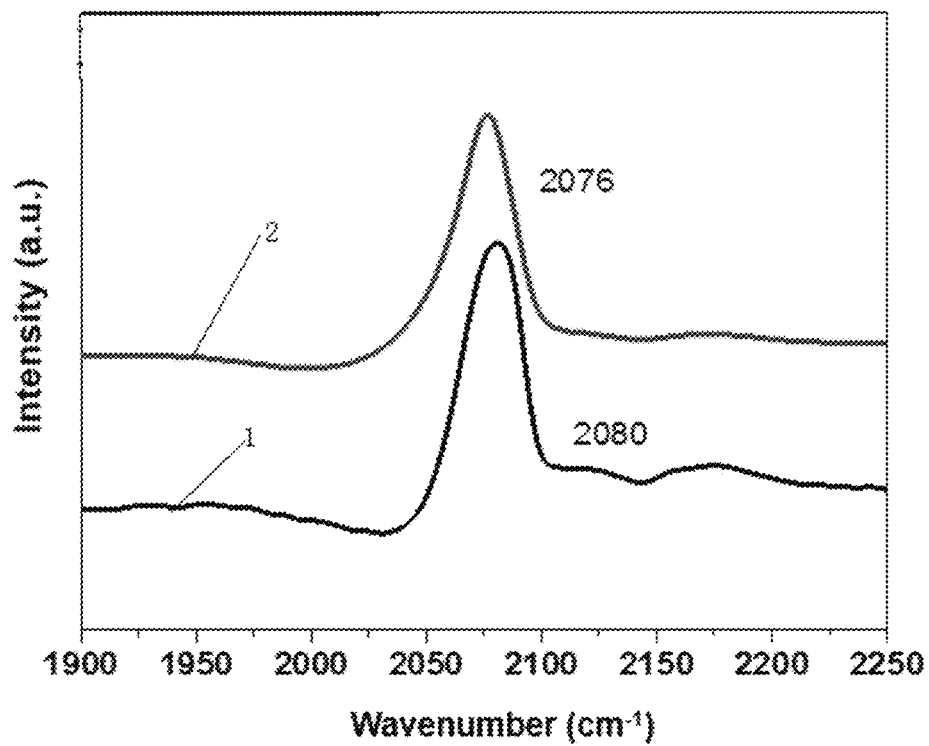
FIG. 6 shows curves of diffuse reflectance infrared Fourier transform spectroscopy of chemisorbed CO (CO-FTIR) of the catalyst in the present invention, where line 1 presents the PtFe@Pt/SBA-15 catalyst of the present invention, and line 2 presents the Pt/SBA-15.
Figure 7:
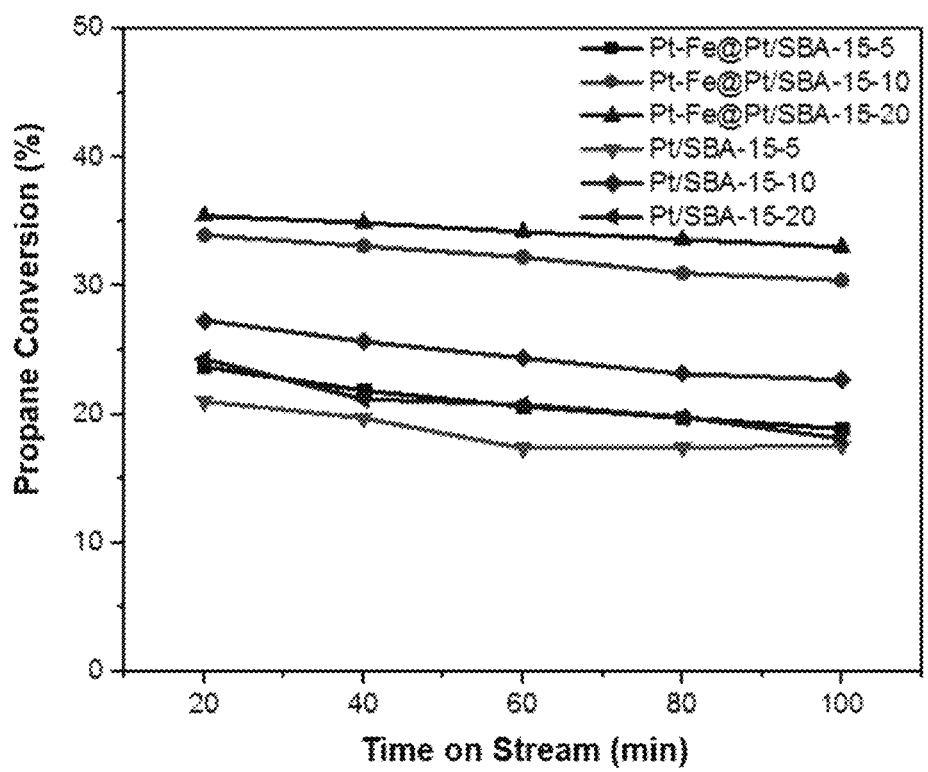
FIG. 7 is a diagram showing a test (propane conversion) of activities of the PtFe@Pt/SBA-15 catalyst and the Pt/SBA-15 catalyst over different acid leaching times, where the different acid leaching times are respectively 5 minutes, 10 minutes, and 20 minutes.
Figure 8:
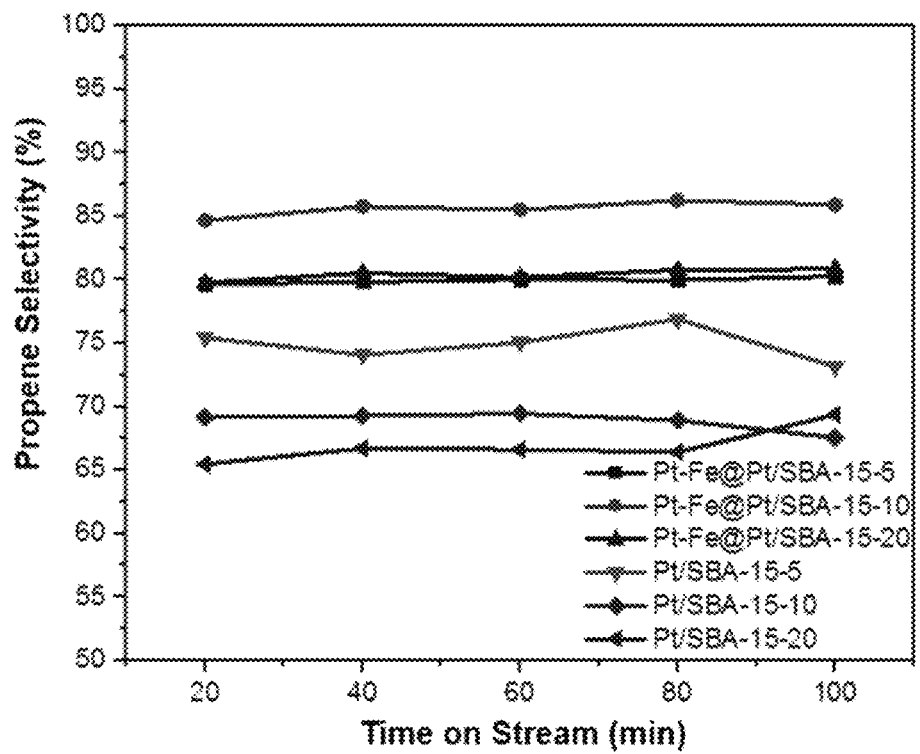
FIG. 8 is a diagram showing a test (propylene selectivity) of activities of the PtFe@Pt/SBA-15 catalyst and the Pt/SBA-15 catalyst over different acid leaching times, where the different acid leaching times are respectively 5 minutes, 10 minutes, and 20 minutes.
Figure 9:
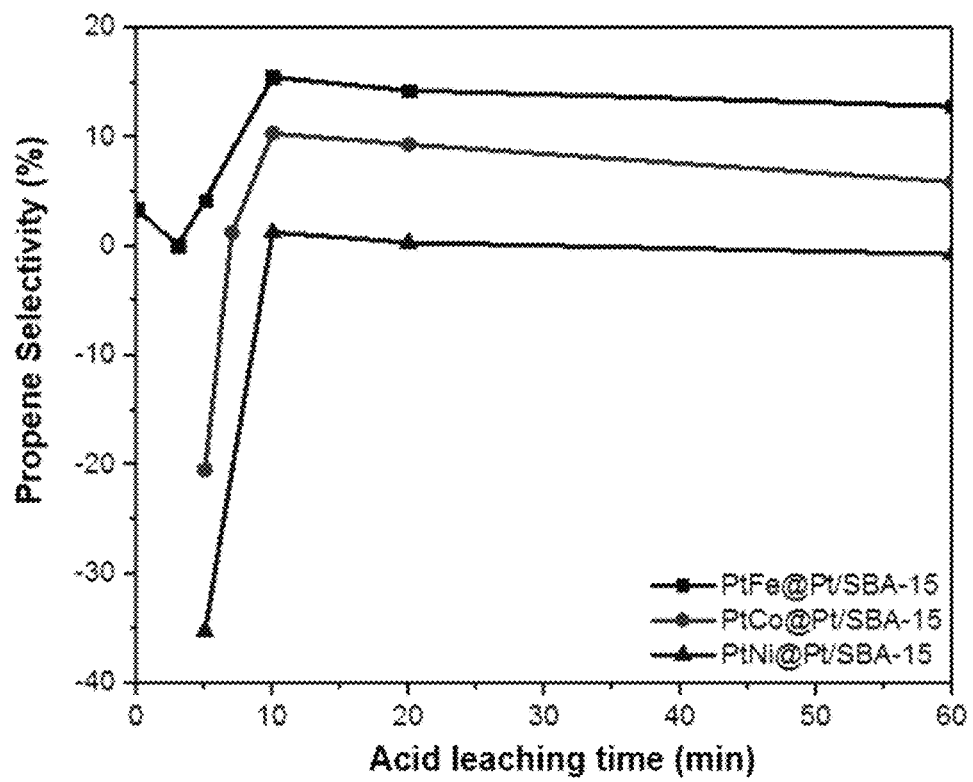
FIG. 9 is a schematic diagram showing the different values of propylene selectivity between Pt-3d@Pt/SBA-15 (3d is Fe, Co or Ni) and Pt/SBA-15 at different acid leaching times and different 3d transition metals, where the propylene selectivity of the Pt-3d@Pt/SBA-15 is higher than that of the Pt/SBA-15 at the same acid leaching time.
Figure 10:
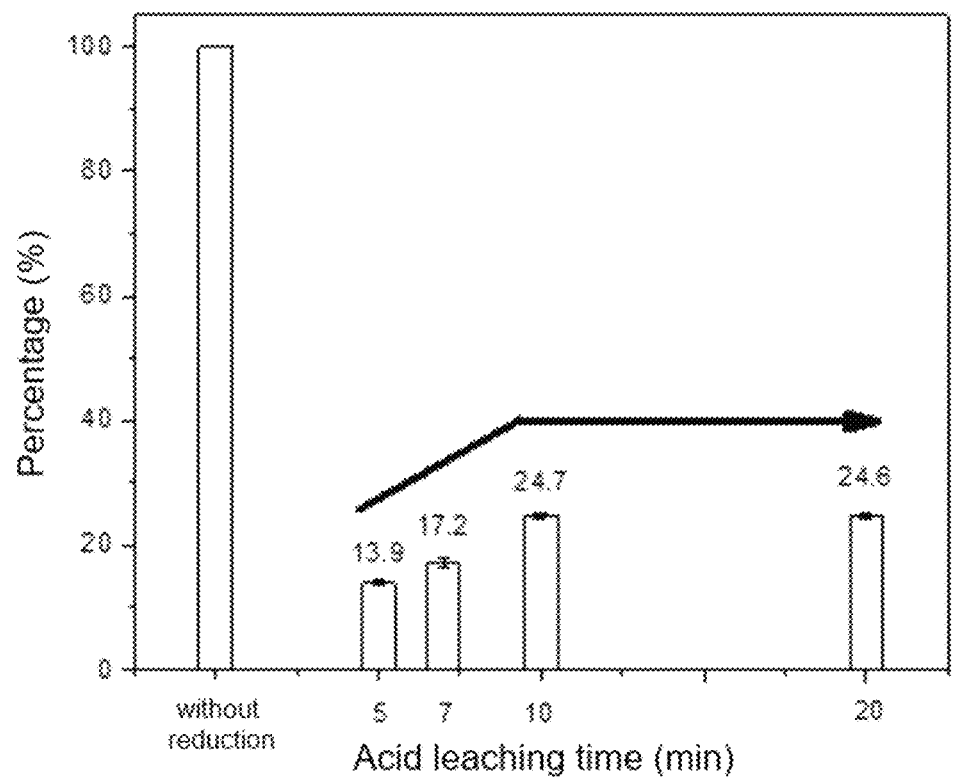
FIG. 10 is a diagram showing a change curve of percentages of leached out 3d metal (e.g., Fe) in the catalyst of the present invention over acid leaching time, where the abscissa is timed in minutes, and the ordinate is the molar ratio of the leached out 3d metal to the initial 3d metal (i.e., the mole percentage of the 3d metal that is leached out).

The Pt/SBA-15 catalyst was prepared by the preparation method of the present invention without adding the 3d metal. The PtFe@Pt/SBA-15 is the catalyst of the present invention. As shown in TABLE 1, after adding Fe, the total selectivity of the surface Pt atoms for propylene is indeed improved. This indicates that the addition of Fe downshifts the d-band center of the surface Pt atoms by the electronic effect and the lattice effect, and weakens its adsorption to propylene, thereby effectively improving the selectivity of the surface Pt atoms for propylene compared with pure Pt. That is, the catalyst having a relatively high selectivity for propylene and relatively low usage amount of Pt is obtained. From the XRD characterization, after the addition of Fe, the overall crystal form of the catalyst did not change significantly, and the peak position shift for the Fe element was presented. FIG. 4 shows an XPS bond energy peak of the 2p orbital of the Fe element before and after acid leaching. FIG. 4 shows that after acid leaching, the peak energy of the 2p orbital of Fe is 707.9 ev, while the peak of the 2p orbital of Fe before acid leaching is 709.9 ev. It can be seen that the peak of the 2p orbital of Fe is shifted to a higher energy before acid leaching than after acid leaching, indicating that the Fe element is in an oxidation state at this time. Before acid leaching, since Fe is still presented on the surface of the particles, it is easily oxidized in the air, thus exhibiting the oxidation state. After acid leaching, since Fe is presented in the inner core, it can be protected by the surface Pt, so that it is not oxidized, thereby presenting a metallic state. Therefore, from the XPS diagram, the synthesized catalyst having a structure where Pt is enriched on the surface is finally obtained. The characterization instrument used in XPS is the PHI 1600 ESCA instrument manufactured by Physical Electronics (PE) Company, and its X-ray source uses an Al target (hv=1486.6 eV).

The instrument used in an inductively coupled plasma (ICP) test was inductively coupled plasma atomic emission spectrometry (ICP-MS) (7700x, Agilent) manufactured by Agilent. The test was performed by diffusing reflectance infrared Fourier transform spectroscopy of chemisorbed CO (CO-DRIFTS) and temperature-programmed desorption of propylene ($C_3H_6$-TPD). The temperature was ramped from 100° C. to 800° C. with a ramp rate of 10° C./min). It is found that after adding the 3d metal, the number of waves increased, the position of the peak changed, indicating that the d-band center of the surface metal Pt was downshifted, resulting in a decrease in adsorption capacity. When the catalyst of the present invention was subjected to acid leaching, as shown in the figure, the amount of Fe atoms leached out showed a tendency of first increase and then basically was constant with the increase of the acid leaching time. In the first 10 minutes, as the acid leaching time increased, the amount of Fe atoms leached out was gradually increased. At the tenth minute, the Fe atoms were leached out by about 24.7% (maintaining 75% of the Fe atoms in the initial charge). Then, although the acid leaching time was increased, the amount of the Fe atoms leached out was no longer increased. This further shows that the final obtained catalyst still has Fe atoms, and the Fe atoms are not completely leached out.

Figure 11:
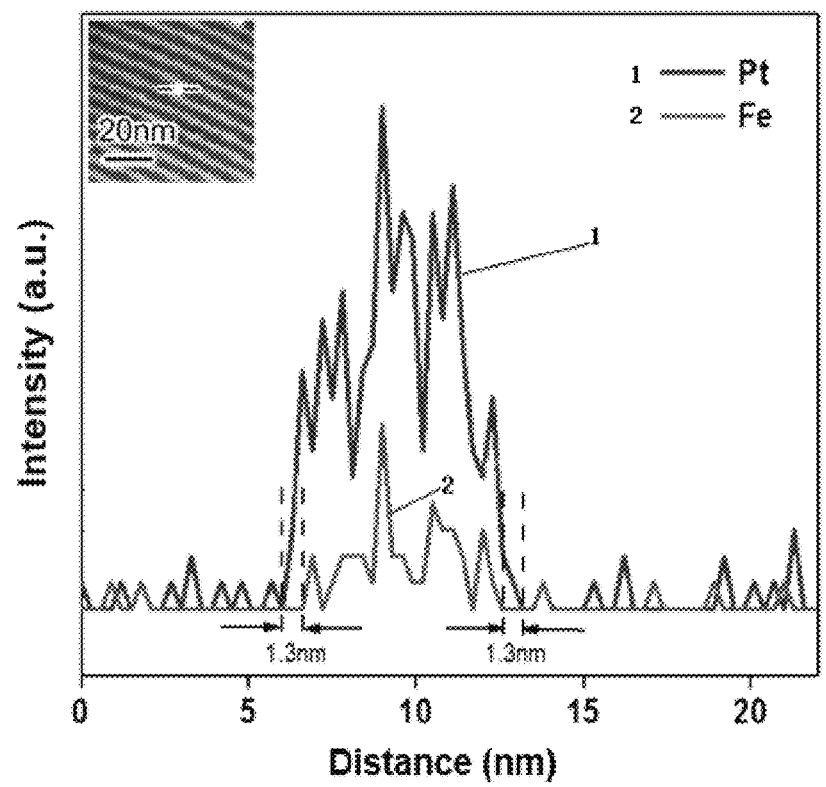
FIG. 11 shows an energy-dispersive spectroscopy (EDS) of the catalyst before and after acid leaching in the present invention, where line 1 presents metal Pt, and line 2 presents metal Fe.
Figure 12:
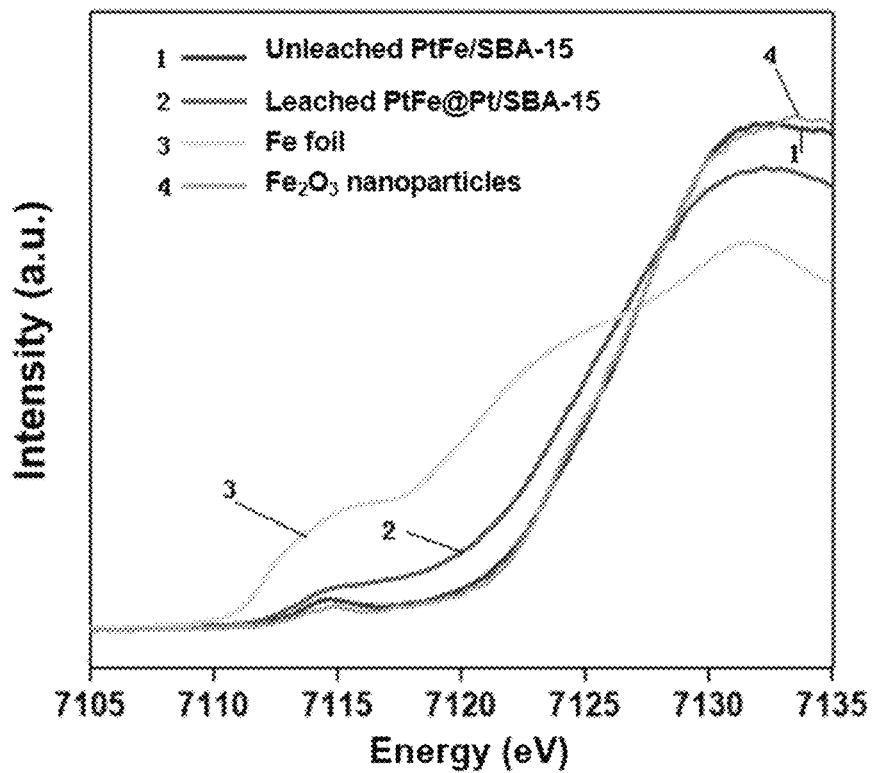
FIG. 12 shows X-ray absorption near-edge structures (XANES) of the catalyst before and after acid leaching, where line 1 presents PtFe/SBA-15 before acid leaching, line 2 presents PtFe/SBA-15 after acid leaching, line 3 presents Fe foil, and line 4 presents Fe$_2$O$_3$ nanoparticle.

The catalysts before and after acid leaching (PtFe/SBA-15 before acid leaching, PtFe@Pt/SBA-15 after acid leaching) were determined by X-ray absorption near-edge structure (XANES). The results of Fe K-edge XANES study on the catalyst sample before acid leaching are shown in FIG. 12. Meanwhile, for better illustrating this problem, the spectra of $Fe_2O_3$ nanoparticles and standard metal Fe foil were also used as reference. It is generally believed that the peaks of the adsorption energies of 7115 eV and 7132 eV in the Fe K-edge XANES correspond to the electronic transitions from 1s to 3d orbits and the electronic transitions from 1s to 4p orbits of Fe atoms, respectively. FIG. 12 shows that before acid leaching, the Fe K-edge XANES of the PtFe/SBA-15 catalyst sample is similar to that of $Fe_2O_3$, and the peak intensity of the white line of the absorption near-edge is relatively high due to the Fe—O interaction. However, after acid leaching, the peak intensity of the white line of the Fe K absorption edge of the obtained PtFe@Pt catalyst decreases, the position of the absorption edge shifts to a lower energy, and its spectral structure is similar to that of the metal Fe foil. Therefore, in response to the XPS results, when the catalyst is exposed to the air before acid leaching, the surface Fe atoms are oxidized by oxygen in the air to change from a metallic state to an oxidation state. Conversely, after acid leaching, the Fe atoms are protected from being oxidized by oxygen in the air. The XANES study results further support the formation of the structure where subsurface is modified by Fe and surface is enriched with Pt, which are consistent with the results of ICP and XPS, namely, the final data after high temperature reduction and acid leaching. The core-shell structure with Pt enriched on the surface was obtained, which is the catalyst with the PtFe@Pt core-shell structure. In order to directly confirm the formation of the structure where subsurface is modified by the 3d transition metal and surface is enriched with Pt, the EDS spectrum of the finally obtained PtFe@Pt catalyst after acid leaching is provided in FIG. 11. On both sides of the nanoparticles, the signal of Pt appeared earlier than that of Fe, indicating the formation of the Pt skin structure. Meanwhile, it can be seen that the thickness of the Pt skin is an average of 1.3 nm, which is equal to the thickness of about 3-5 atomic layers of Pt.

Embodiment 2

The reaction was carried out by the same manner as described in embodiment 1, except that, in step (5), the catalyst, after ultrasonically shaking in the dilute nitric acid solution, was left to rest for a time of 5 minutes. The obtained catalyst was PtFe@Pt/SBA-15, which was acid leached for 5 minutes.

Embodiment 3

The reaction was carried out by the same manner as described in embodiment 1, except that, in step (5), the catalyst, after ultrasonically shaking in the dilute nitric acid solution, was left to rest for a time of 20 minutes. The obtained catalyst was PtFe@Pt/SBA-15 min, which was acid leached for 20 minutes.

Embodiment 4

The reaction was carried out by the same manner as described in embodiment 1, except that, in step (5), the catalyst, after ultrasonically shaking in the dilute nitric acid solution, was left to rest for a time of 60 minutes. The obtained catalyst was PtFe@Pt/SBA-15 min, which was acid leached for 60 minutes.

Embodiment 5

The reaction was carried out by the same manner as described in embodiment 1, except that, in step (5), the acid leaching in the nitric acid solution was deleted, and the obtained catalyst was PtFe@Pt/SBA-15 without acid leaching.

Embodiment 6

The reaction was carried out by the same manner as described in embodiment 1, except that, in step (1), the 3d transition metal was $Co(NO_3)_2$ with the mass ratio of Pt to Co of 3:1. Moreover, in step (5), the catalyst, after ultrasonically shaking in the dilute nitric acid solution, was left to rest for a time of 5 minutes. The obtained catalyst was PtCo@Pt/SBA-15, which was acid leached for 5 minutes.

Embodiment 7

The reaction was carried out by the same manner as described in embodiment 6, except that, in step (5), the catalyst, after ultrasonically shaking in the dilute nitric acid solution, was left to rest for a time of 10 minutes. The obtained catalyst was PtCo@Pt/SBA-15 min, which was acid leached for 10 minutes.

Embodiment 8

The reaction was carried out by the same manner as described in embodiment 6, except that, in step (5), the catalyst, after ultrasonically shaking in the dilute nitric acid solution, was left to rest for a time of 20 minutes. The obtained catalyst was PtCo@Pt/SBA-15 min, which was acid leached for 20 minutes.

Embodiment 9

The reaction was carried out by the same manner as described in embodiment 6, except that, in step (5), the catalyst, after ultrasonically shaking in the dilute nitric acid solution, was left to rest for a time of 60 minutes. The obtained catalyst was PtCo@Pt/SBA-15 min, which was acid leached for 60 minutes.

Embodiment 10

The reaction was carried out by the same manner as described in embodiment 1, except that, in step (1), the 3d transition metal was Ni(NO$_3$)$_2$ with the molar ratio of Pt to Ni of 3:1. Moreover, in step (5), the catalyst, after ultrasonically shaking in the dilute nitric acid solution, was left to rest for a time of 5 minutes. The obtained catalyst was PtNi@Pt/SBA-15, which was acid leached for 5 minutes.

Embodiment 11

The reaction was carried out by the same manner as described in embodiment 10, except that, in step (5), the catalyst, after ultrasonically shaking in the dilute nitric acid solution, was left to rest for a time of 10 minutes. The obtained catalyst was PtNi@Pt/SBA-15, which was acid leached for 10 minutes.

Embodiment 12

The reaction was carried out by the same manner as described in embodiment 10, except that, in step (5), the catalyst, after ultrasonically shaking in the dilute nitric acid solution, was left to rest for a time of 20 minutes. The obtained catalyst was PtNi@Pt/SBA 15 min, which was acid leached for 20 minutes.

Embodiment 13

The reaction was carried out by the same manner as described in embodiment 10, except that, in step (5), the catalyst, after ultrasonically shaking in the dilute nitric acid solution, was left to rest for a time of 60 minutes. The obtained catalyst was PtNi@Pt/SBA 15 min, which was acid leached for 60 minutes.

With regard to the results and data of the above embodiments, for such a core-shell Pt3d@Pt/SBA-15 (3d is Fe, Co or Ni) catalyst supported on SBA-15, the effect of the catalysts formed by different 3d transition metals and through different acid leaching times, the selectivity for propylene during the dehydrogenation of propane was investigated.

(1) The effect of different acid leaching times on the selectivity for propylene during the dehydrogenation of propane, referring to TABLE 2.

TABLE 2

Effect of different values of propylene selectivity between the catalysts formed by adding different 3d transition metals into subsurface with different acid leaching time and Pt/SBA-15

| Acid leaching time (min) | PtFe@Pt/SBA-15 | PtCo@Pt/SBA-15 | PtNi@Pt/SBA-15 |
|---|---|---|---|
| 5 | 4% | −20% | −35% |
| 10 | 16% | 10% | 1% |
| 20 | 14% | 9% | 0.3% |
| 60 | 13% | 6% | −0.7% |

First, from the longitudinal direction of the table, it can be seen that, compared to Pt/SBA-15, with the increase of the acid leaching time, the propylene selectivity of the core-shell Pt3d@Pt/SBA-15 (3d is Fe, Co or Ni) catalyst supported on the SBA-15 presents a tendency of first increase, and then basically constant. The PtFe@Pt/SBA-15 reached the maximum when the acid leaching time was 10 minutes. This demonstrates that, the d-band center of the surface Pt is downshifted by the addition of the 3d transition metal, thereby improving the selectivity for propylene.

Second, from the lateral direction of the table, it can be seen that, compared to pure Pt, the addition of different 3d transition metals shows some difference in the improvement of propylene selectivity. As can be seen from the table, the extent of increasing the selectivity for propylene is increased in the row: PtFe/SBA-15>PtCo/SBA-15>PtNi/SBA-15. This indicates that the addition of different 3d transition metals makes different electronic effects and geometric effects on the surface Pt, and therefore the degree of the downshift of the d-band center of the Pt atoms is also different. Thus, the selectivity for propylene is different as well. Moreover, it can be seen that the PtCo/SBA-15 and PtNi/SBA-15 core-shell catalysts have a particularly low selectivity for propylene when the acid leaching time is 5 minutes, because Co and Ni break the carbon-carbon bond before the core-shell structure is formed, thereby reducing the selectivity for propylene.

The catalyst of the present invention can be prepared by adjusting parameters according to the raw material formulation and preparation process. The prepared catalyst shows similar performance to the catalysts of the embodiments. The present invention has been described in detail above. It should be noted that any simple modifications, alterations, or other equivalents obtained by those skilled in the art without creative work and without departing from the core concept of the present invention fall within the scope of the present invention.

What is claimed is:

1. A supported core-shell bimetallic catalyst having a high selectivity,
comprising: a metal Pt, a 3d metal, and a support, wherein the metal Pt and the 3d metal are loaded onto the support, wherein for a mass of the support of 100 wt %, a content of the metal Pt ranges from 0.5 wt % to 1 wt %, the mole ratio of the metal Pt to the 3d metal is (3-5):(1-1.5), a shell layer composed of the metal Pt is formed on a surface of the supported core-shell bimetallic catalyst, an inner core composed of the metal Pt and the 3d metal is formed in the supported core-shell bimetallic catalyst, and from the surface to the inner core, the content distribution of the metal Pt gradually decreases, and the content distribution of the 3d metal gradually increases; and the 3d metal is Fe, Co or Ni, wherein the support is commercial Santa Barbara Amorphous-15 (SBA-15).

2. The supported core-shell bimetallic catalyst having the high selectivity of claim 1, wherein, the content of the metal Pt ranges from 0.75 wt % to 0.8 wt %, and the mole ratio of the metal Pt to the 3d metal is 3:(0.75-0.85).

3. A method for preparing a supported core-shell bimetallic catalyst having a high selectivity, comprising the following steps:

step 1, providing a support and an impregnation system, wherein the impregnation system comprises a solvent and metal precursors, wherein the solvent comprises deionization water and ethanol, and wherein the metal precursors provide a metal Pt and a 3d metal;

step 2, adding the support to the impregnation system and then stirring and impregnating until the solvent in the impregnation system evaporates to load the metal Pt and the 3d metal on the support in the impregnation system; wherein the 3d metal is Fe, Co or Ni; a volume ratio of deionization water to ethanol is (1-2):(1-3); in the aqueous of metal precursors, the mole ratio of the metal Pt to the 3d metal is (3-5):(1-1.5); for a mass of the support of 100 wt %, a content of the metal Pt ranges from 0.5 wt % to 1 wt %;

step 3, drying the support loaded with the metal Pt and the 3d metal, and then calcining in air to form metal oxides at 300-350° C. for 2-4 hours with a ramp rate of 2-5° C./min from the room temperature of 20-25° C.;

step 4: performing a high temperature reduction on the support in the step 2 in an atmosphere of hydrogen and argon at 400-450° C. for 4-6 hours with a ramp rate of 2-5° C./min from the room temperature of 20-25° C. to obtain a high temperature reduced catalyst; wherein in a mixed gas of the atmosphere of hydrogen and argon, the volume percentage of hydrogen is 5-10%; the metal Pt tends to enrich the surface of the support, and the 3d metal tends to enrich in the core of the support; from the surface to the core of the support, the metal Pt exhibits an opposite distribution trend to the 3d metal; wherein, the content distribution of the metal Pt gradually decreases, and the content distribution of the 3d metal gradually increases; and step 5: performing an acid treatment on the high temperature reduced catalyst in the step 3 to remove the 3d metal at the surface of the support, thereby forming a shell layer composed of the metal Pt and the inner core composed of the metal Pt and the 3d metal, wherein, in the step 1, the support is commercial Santa Barbara Amorphous-15 (SBA-15), and the stirring and impregnating are performed by a mechanical or ultrasonic agitator for 20-24 hours, with a speed of 200-300 revolutions per minute at 20-25° C.

4. The method for preparing the supported core-shell bimetallic catalyst having the high selectivity of claim 3, wherein, in the step 1, the volume ratio of deionization water to ethanol is 1:1; in the aqueous of metal precursors, the mole ratio of the metal Pt to the 3d metal is 3:(1-1.5) or (3-5):1; for the mass of the support of 100 wt %, the content of platinum ranges from 0.75 wt % to 0.8 wt %.

5. The method for preparing the supported core-shell bimetallic catalyst having the high selectivity of claim 3, wherein, in the step 4, an acid used in the acid treatment dissolves the 3d metal but does not react with the metal Pt.

6. The method for preparing the supported core-shell bimetallic catalyst having the high selectivity of claim 5, wherein, in the step 4, the acid for the acid treatment is a dilute nitric acid solution with a concentration of $5 \times 10^{-4}$ mol/L.

7. The method for preparing the supported core-shell bimetallic catalyst having the high selectivity of claim 3, wherein, in the step 4, the acid treatment is performed at 20-25° C. and lasts 1-20 minutes.

8. The method for preparing the supported core-shell bimetallic catalyst having the high selectivity of claim 7, wherein, in the step 4, the acid treatment is performed at 20-25° C. for 10-20 minutes.

9. A method of propane dehydrogenation, comprising: mixing the supported core-shell bimetallic catalyst having the high selectivity of claim 1 with propane in the propane dehydrogenation to produce propylene.

10. The method of propane dehydrogenation of claim 9, wherein, during use, the supported core-shell bimetallic catalyst is subjected to a pelleting treatment to obtain a granular catalyst having a 20-40 mesh size distribution for subsequent use.

11. The method of propane dehydrogenation of claim 9, wherein, during use, the supported core-shell bimetallic catalyst is loaded into a reactor, a mixed gas of nitrogen and hydrogen is introduced, a temperature in the reactor is increased from room temperature of 20-25° C. to 600-620° C. with a ramp rate of 3-5° C./min, and a reduction is performed at 600-620° C.; after the reduction, the temperature in the reactor is controlled to be 550-650° C., propane is introduced into the reactor at a weight hourly space velocity of 3-10 $h^{-1}$ for reaction, wherein the molar ratio of propane to hydrogen is 1:1, nitrogen is used as equilibrium gas, and a volume ratio of propane, hydrogen and nitrogen is 7:7:11.

12. The method of propane dehydrogenation of claim 11, wherein, during use, the reduction lasts at least for 0.5 hour, and in the mixed gas of nitrogen and hydrogen, the hydrogen is 10-15% by volume.

13. The method of propane dehydrogenation of claim 11, wherein, during use, the reduction lasts for 1-2 hours.

* * * * *